(12) United States Patent
Cotting et al.

(10) Patent No.: US 7,090,678 B2
(45) Date of Patent: Aug. 15, 2006

(54) POSITIONING INSTRUMENT FOR INSERTING AN EXTENSION SHELL

(75) Inventors: Anton Cotting, Grenchen (CH); Peter Christen, Selzach (CH); Daniel Delfosse, Bern (CH)

(73) Assignee: Mathys Medizinaltechnik AG, Bettlach (CH)

( * ) Notice: Subject to any disclaimer, the term of this patent is extended or adjusted under 35 U.S.C. 154(b) by 301 days.

(21) Appl. No.: 10/469,450

(22) PCT Filed: Feb. 26, 2002

(86) PCT No.: PCT/EP02/02039

§ 371 (c)(1),
(2), (4) Date: Aug. 29, 2003

(87) PCT Pub. No.: WO02/074203

PCT Pub. Date: Sep. 26, 2002

(65) Prior Publication Data

US 2004/0073226 A1    Apr. 15, 2004

(30) Foreign Application Priority Data

Mar. 15, 2001 (DE) .................... 101 12 527

(51) Int. Cl.
*A61B 17/00* (2006.01)
(52) U.S. Cl. .................................................. 606/81
(58) Field of Classification Search .......... 606/79, 606/80, 99, 100
See application file for complete search history.

(56) References Cited

U.S. PATENT DOCUMENTS

| | | | | |
|---|---|---|---|---|
| 2,574,352 A | * | 11/1951 | Senter .................. 81/125 |
| 4,271,849 A | * | 6/1981 | Rehder .................. 606/81 |
| 4,305,394 A | * | 12/1981 | Bertuch, Jr. ............ 606/91 |
| 4,462,395 A | * | 7/1984 | Johnson ................. 606/75 |
| 4,662,891 A | * | 5/1987 | Noiles ................. 623/22.31 |
| 4,716,894 A | * | 1/1988 | Lazzeri et al. ........... 606/91 |
| 5,037,424 A | * | 8/1991 | Aboczsky ............... 606/91 |
| 5,098,437 A | * | 3/1992 | Kashuba et al. .......... 606/89 |
| 5,236,433 A | * | 8/1993 | Salyer .................. 606/91 |
| 5,320,625 A | | 6/1994 | Bertin |
| 5,474,560 A | | 12/1995 | Rohr, Jr. |
| 5,540,697 A | * | 7/1996 | Rehmann et al. ......... 606/91 |

(Continued)

FOREIGN PATENT DOCUMENTS

DE            692 00 367 T2     12/1994

(Continued)

*Primary Examiner*—Eduardo C. Robert
*Assistant Examiner*—Mary C Hoffman
(74) *Attorney, Agent, or Firm*—Scully, Scott, Murphy & Presser, P.C.

(57) ABSTRACT

The invention relates to a positioning instrument (1) for inserting an extension shell (2) into a human or animal bone, especially a pelvic bone. Said instrument comprises a fixing device (18) for fixing the extension shell (2) to the positioning instrument (1), and a displacement device (55) for displacing a disc element (15) of the positioning instrument (1) at least essentially axially in relation to the extension shell (2) fixed to the fixing device (18). Said disc element (15) co-operates with beveled surfaces (25a to 25e) of the extension shell (2) during the displacement, in order to tighten the extension shell (2). Furthermore, the disc element (15)-viewed in the direction of insertion (13)-does not project beyond the radially furthest projecting elements (32a, 32b) of the tightened extension shell (2).

5 Claims, 2 Drawing Sheets

U.S. PATENT DOCUMENTS

| | | | |
|---|---|---|---|
| 5,658,290 A * | 8/1997 | Lechot | 606/80 |
| 5,904,688 A | 5/1999 | Gilbert et al. | |
| 5,976,148 A | 11/1999 | Charpenet et al. | |
| 5,989,259 A * | 11/1999 | Penenberg et al. | 606/99 |
| 6,004,326 A * | 12/1999 | Castro et al. | 606/99 |
| 6,042,582 A * | 3/2000 | Ray | 606/61 |
| 6,379,363 B1 * | 4/2002 | Herrington et al. | 606/79 |
| 6,695,850 B1 * | 2/2004 | Diaz | 606/91 |
| 6,854,742 B1 * | 2/2005 | Salyer et al. | 279/93 |
| 2002/0116007 A1 * | 8/2002 | Lewis | 606/99 |
| 2005/0149047 A1 * | 7/2005 | Parry et al. | 606/99 |

FOREIGN PATENT DOCUMENTS

| | | |
|---|---|---|
| DE | 692 18 096 T2 | 7/1997 |
| DE | 196 28 193 C2 | 1/1998 |
| DE | 198 52 687 C1 | 9/2000 |
| EP | 0 169 978 | 2/1986 |
| EP | 0 242 633 B1 | 10/1987 |
| FR | 2 710 522 | 4/1995 |
| GB | 2 299 758 A | 10/1996 |

* cited by examiner

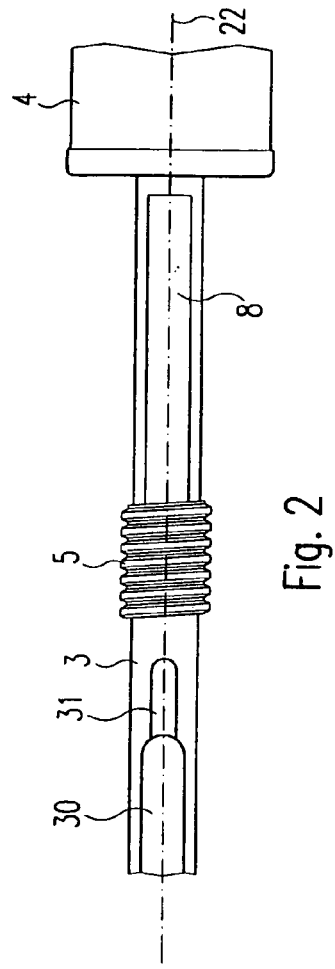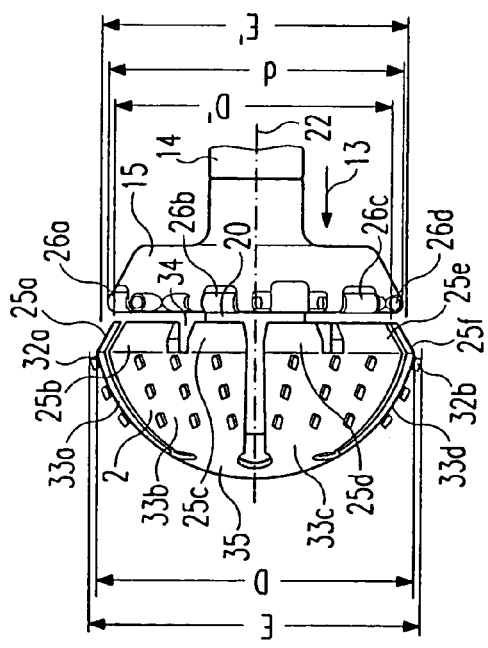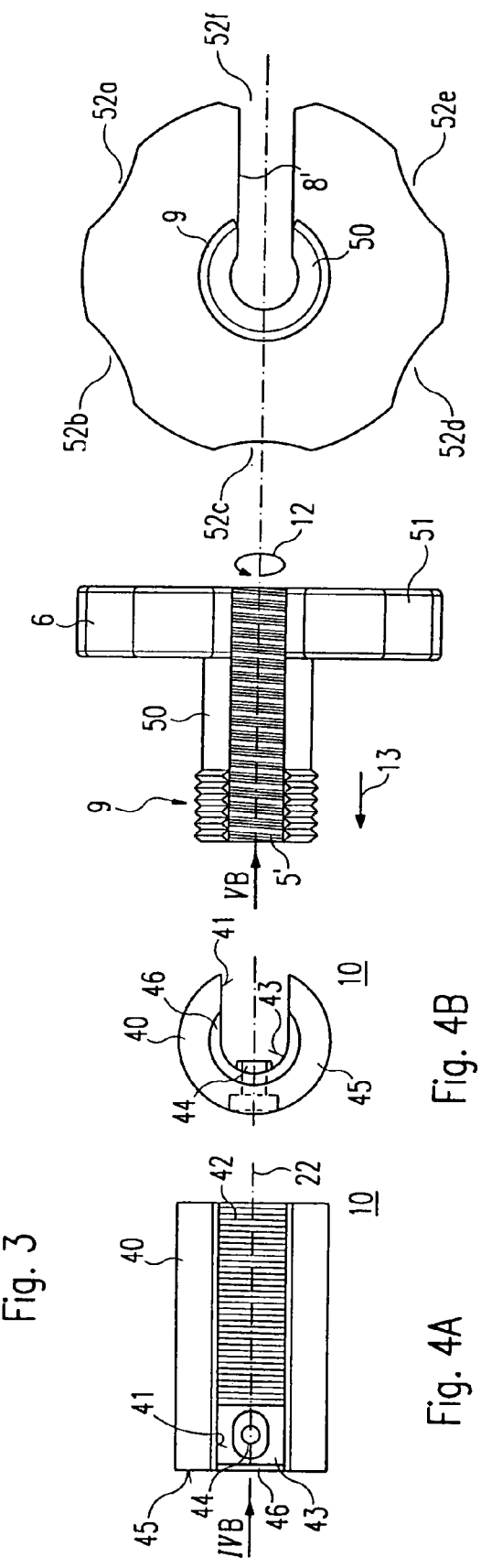

POSITIONING INSTRUMENT FOR INSERTING AN EXTENSION SHELL

The invention relates to a positioning instrument for inserting an extension shell into a human or animal bone. The invention in particular relates to a positioning instrument for inserting an extension shell, which is part of an endoprothesis for a hip joint, into the pelvic bone.

EP 0 242 633 B1 discloses an extension bowl as an endoprosthesis for a hip joint socket for cementless fixation in a pelvic bone. In the case of this known extension bowl first the extension shell is flexibly pressed together with the aid of a tool and then inserted in an axial direction into an operatively created recess in the pelvic bone. Suitable forceps or similar presently serve as the usual tool.

The known method for inserting an extension shell by means of forceps or similar however has several disadvantages. Since the inserting tool surrounds the extension shell laterally, there is a danger when inserting the extension shell of the surrounding bone tissue being damaged. Furthermore removal of the inserting tool presents difficulty, since due to the adjacent bone tissue the inserting tool can only be partly opened, so that when the tool is pulled out the extension shell can easily slip and/or the adjacent bone tissue is damaged. In addition the operating physician has to manipulate the inserting tool in direct proximity of the pelvic bone, as a result of which the necessary insertion force is difficult to apply and ergonomic working is not possible.

In practice insertion of an extension shell is therefore complex and bound up with substantial risks. Also in particular when the extension shell relaxes, the thrust forces necessary for complete insertion of the extension shell into the bone in an axial direction, could up till now only be applied insufficiently.

The object of the invention is to create a positioning instrument which facilitates insertion into the bone and with which a reliable seat of the implanted extension shell can be achieved, so that when the positioning instrument is removed later slipping of the extension shell or damage to the surrounding bone material is prevented.

The object is achieved by a positioning instrument with the features of claim 1. Advantageous further embodiments of the invention are possible through the measures indicated in the sub-claims.

The positioning instrument according to the invention has the advantage that the extension shell can be compressed with the disc element of the positioning instrument, that is to say tightened, without the positioning instrument surrounding the extension shell circumferentially. As a result the positioning instrument is prevented from damaging the surrounding bone tissue, when the extension shell is inserted into the bone. Since the positioning instrument thereby also does not surround the extension shell in the loosened, that is to say extended condition, the positioning instrument can be removed particularly easily. In addition the positioning instrument does not project radially beyond the radially furthest projecting elements of the tightened extension shell, so that it is possible to insert the positioning instrument together with the extension shell in each case.

It is advantageous that the disc element comprises rotatably mounted rollers which, when the extension shell is tightened, roll on the bevelled surfaces of the extension shell. Thus the positioning instrument is preserved, since any abrasion in the vicinity of the disc element acting on the extension shell is prevented. In addition the friction forces are decreased when tightening and relaxing the extension shell, as a result of which lesser tightening and loosening forces are necessary, so that in order to displace the disc element of the positioning instrument lesser displacement forces are necessary. Instead of the rollers rolls, rolling bodies, rolling members or similar can also be used, whereby the rollers or the rolling members have the advantage that the force for tightening the extension shell is transmitted over a greater surface area.

In an advantageous way the displacement device comprises a threaded wheel, which acts by means of a spacer on the disc element. As a result of the threaded wheel the spacer can be pre-tightened in simple way and again relaxed after the inserting, whereby due to the spacer, easier working is permitted, in particular at a distance from the patient. The action of the disc element on the spacer in this case can be assisted by a lifting translation device, which permits tightening and loosening of the extension shell with less force.

The invention is described in more detail below on the basis of an embodiment with reference to the drawing, wherein:

FIG. 2 shows a cutout section of the base of the positioning instrument represented in FIG. 1;

FIG. 3 shows the cutout section designated as III in FIG. 1;

FIG. 4A shows in detail the transmission case of the positioning instrument represented in FIG. 1;

FIG. 4B shows the transmission case shown in FIG. 4A in a front view from the direction designated as IV B in FIG. 4A;

FIG. 5A shows in detail the threaded wheel of the positioning instrument represented in FIG. 1, and FIG. 5B the threaded wheel represented in 5A in a front view from the direction designated as V B in FIG. 5A.

Figure 1:
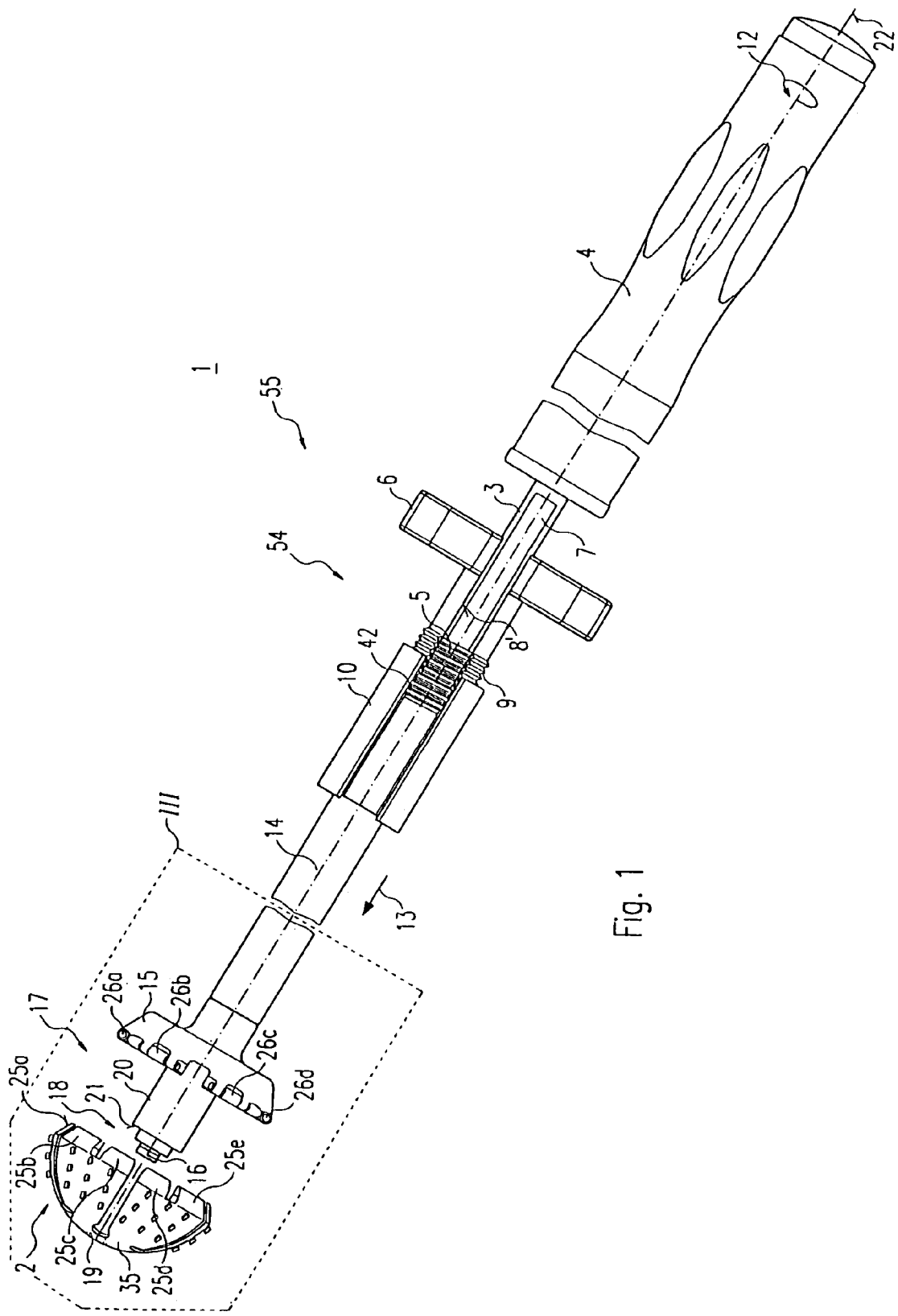
FIG. 1 shows an embodiment of a positioning instrument together with an extension shell.

FIG. 1 shows an embodiment of the positioning instrument 1 according to the invention together with an extension shell 2. The positioning instrument 1 serves to insert the extension shell 2 into a human or animal bone. In particular the positioning instrument 1 serves to insert an extension shell 2, which is part of an endoprothesis for a hip joint, into the pelvic bone.

The positioning instrument 1 comprises a base 3, to which a handle 4 is fixed. The base 3 has a thread 5 formed as trapezoidal thread, on which a threaded wheel 6 is attached. In order to permit attachment of the threaded wheel 6 on the base 3, two opposing faces 7, 8 are formed on the base 3, whereby in FIG. 1 only the face 7 is represented, along which the threaded wheel 6 can be pushed up over the groove-shaped recess formed on the threaded wheel 6. An external thread 9, which engages an internal thread 42 formed on a transmission case 10, is formed on the threaded wheel 6. The transmission case 10 is axially arranged, so that a rotation of the transmission case 10 around the longitudinal axis 12 of the positioning instrument 1 is prevented.

In the case of a rotation of the threaded wheel 6 in the clockwise direction 12 the threaded wheel 6 is screwed into the transmission case 10, so that the transmission case 10 in relation to the threaded wheel 6 is drawn onto the threaded wheel 6, as a consequence of which lifting of the transmission case 10 assisted by the thread 9 results. In addition the threaded wheel 6 is increasingly screwed onto the thread 5, so that lifting of the threaded wheel 6 directed away in relation to the handle 4 results. Lifting of the transmission case 10 is therefore opposed to the lifting concerning the threaded wheel 6. Since the pitch of the thread 5 of the base 3 is greater than the pitch of the external thread 9 of the threaded wheel 6, resultant lifting in the direction of insertion 13 of the transmission case 10 in relation to the base 3 arises. The transmission case 10 transfers this resultant lifting to a spacer 14, whereby a disc element 15 of the positioning instrument 1 is axially displaced in the direction of displacement or insertion 13.

Conversely the disc element 15 is displaced against the direction of insertion 13 as the result of a rotation of the threaded wheel 6 against the clockwise direction 12.

In addition the base 3 has a grub-screw 16, which is provided at the upper end 17 of the positioning instrument 1. The grub-screw 16 is part of a fixing device 18 which serves to fix the extension shell 2 on the positioning instrument 1. The extension shell 2 has a thread 19, with which this can be screwed onto the grub-screw 16. The screwed on extension shell 2 is tightened by displacing the disc element 15 in the direction of insertion 13. The disc element 15 has a case 20, whereby as a result of the front face 21 of the case 20 striking the inner face of the extension shell 2 in the vicinity of the thread 19 the maximum displacement of the disc element 15 and thus the maximum tightening force acting on the extension shell 2 is limited.

For tightening the extension shell 2 the disc element 15 acts on the bevelled surfaces of the extension shell 2, whereby the bevelled surfaces 25a to 25e are represented in FIG. 1. In order to reduce the wear of the disc element 15 of the positioning instrument 1, the disc element 15 has several circumferentially spaced rollers, of which the rollers 26a to 26d are represented in FIG. 1. When the extension shell 2 is tightened the rollers 26a to 26d roll on the corresponding bevelled surfaces 25a to 25e.

FIG. 2 shows a cutout section of the base 3 of the positioning instrument 1 represented in FIG. 1. Elements already described are identified in this and all other drawings with the same reference symbols, as a result of which repeated description is superfluous.

FIG. 2 shows a view onto the base of the positioning instrument 1, which compared to the view represented in FIG. 1 is turned around 180° in relation to the longitudinal axis 22. Therefore the face 8 lying opposite the face 7 is shown in FIG. 2 by the two faces 7, 8, which are formed on the base 3. In addition the base 3 has a recess 30, in which the transmission case 10 engages, and a recess 31 joining it. As a result of the engagement of the transmission case 10 in the recess 30 a rotation of the transmission case 10 around the longitudinal axis 22 of the base 3 is prevented at least up to a certain play, so that axial guidance of the transmission case 10 results, since the recess 30 is formed as a longitudinal groove.

FIG. 3 shows the cutout section of the positioning instrument 1 designated as III in FIG. 1 and the extension shell 2 in the screwed on but relaxed state.

For tightening the extension shell 2 the disc element 15 in the direction of insertion 13 is displaced in relation to the extension shell 2 fixed on the fixing device 18. In this case the disc element 15 acts via the rollers 26a to 26d on the bevelled surfaces 25a to 25f. In order to reduce wear of the disc element 15 and to facilitate tightening of the extension shell 2, the rollers 26a to 26d roll on the surfaces 25a to 25f lying opposite them. For this purpose the disc element 15 can be turned around the longitudinal axis 22, in order to bring the rollers 26a to 26d to a suitable position. In the embodiment shown the roller 26a is arranged opposite the bevelled surface 25a, the roller 26b is arranged opposite the bevelled surface 25c, the roller 26c is arranged opposite the bevelled surface 25e and the roller 26d is arranged opposite the bevelled surface 25f. As a result the rollers 26a to 26d over their entire longitudinal direction contact the bevelled surfaces 25a to 25f, so that uniform transfer of force is ensured.

Alternatively the rollers 26a to 26d in each case may also be arranged between the two bevelled surfaces 25a–25f of a segment 33a–33d for tightening the extension shell 2. 15 Regarding the segment 33b the roller 26b is then arranged opposite the gap 34 between the two surfaces 25b and 25c, so that the roller 26b in each case partly contacts the surface 25b and partly the surface 25c. The roller 26b thereby lies essentially parallel to the axis of rotation, around which the segment 33b during the tightening and relaxing is rotated to a minimum extent. Since the roller 26b in this case engages centrally at the end of the segment 33b, an advantageous transfer of force results, which facilitates radial-symmetrical tightening of the segment 33b.

In the relaxed condition the extension shell 2, apart from individual projections, such as for example the projecting elements 32a and 32b, has the diameter D. That is to say the projection of the base 35 of the extension shell 2 along the longitudinal axis 22 in the direction of insertion 13 essentially corresponds to a circle with diameter D. The disc element 15 essentially has the diameter d, so that the projection of the disc element 15 in the direction of insertion 13 essentially corresponds to a circle with the diameter d. Since the diameter d of the disc element 15 is less than the diameter D of the base 35 of the extension shell 2, the projection of the disc element 15 viewed in the direction of insertion 13 does not project over the projection of the extension shell 2 viewed in the direction of insertion 13 in the relaxed condition.

The diameter d of the disc element 15 is however even selected so much smaller than the diameter D of the extension shell 2 in the relaxed condition that the projection of the disc element 15 also does not project over the projection of the radially projecting elements 32a, 32b of the extension shell 2 in the tightened condition, viewed in the direction of insertion 13. The diameter d of the disc element 15 is therefore less than the diameter E' of the tightened extension shell 2 related to the radially furthest projecting elements 32a, 32b. In this case the diameter D' of the base 35 of the extension shell 2 in the tightened condition is smaller than the diameter D of the base 35 of the extension shell 2 in the relaxed condition.

Thus the following relationship applies:

Diameter d of the disc element 15 < diameter E' of the tightened extension shell 2 related to the radially furthest projecting elements 32a, 32b < diameter E of the relaxed extension shell 2 related to the radially furthest projecting elements 32a, 32b.

Still better conditions can be obtained by the following relationship:

Diameter d of the disc element 15 < diameter D' of the base 35 of the tightened extension shell 2 <' diameter D of the base 35 of the relaxed extension shell 2

Thus the extension shell 2 can be inserted in the tightened condition into the corresponding bone, without there being a danger that the disc element 15 of the positioning instrument 1 remains hanging on parts of the body, since elements of the extension shell 2, namely the radially furthest projecting elements 32a, 32b, project radially over the projection of the disc element which is viewed in the direction of insertion 13 so that the disc element 15 can be inserted and afterwards removed again through the channel necessary for the extension shell 2.

In addition there is also no danger, when the positioning instrument 1 is removed after the extension shell 2 has been inserted into the bone, that the extension shell 2 slips, since by loosening the disc element 15 against the direction of insertion 13 in relation to the extension shell 2 the displacement force for tightening the extension shell 2 is uniformly reduced circumferentially, as a result of which the individual segments 33a to 33d of the extension shell 2 relax evenly. In this case it is to be noted that one of the rollers 26a to 26d acts on every one of the segments 33a to 33d of the extension shell 2 since for example, with the segment 33b of the extension shell 2, the roller 26b of the disc element 15 acts on the bevelled surface 25c of the extension shell 2. It is however also possible that, in order to remain with the segment 33b, a roller of a correspondingly modified disc element 15 in each case acts on both the bevelled surface 25c and the bevelled surface 25b.

FIG. 4A shows in detail the transmission case 10 represented in FIG. 1. The transmission case 10 consists of a tubular base 40, which has a slit-shaped recess 41. As a result of the slit-shaped recess 41 the tubular base 40 can also be attached from the side on the base 3 of the positioning instrument 1. The tubular base 40 of the transmission case 10 has, in sections, an internal thread 42 in which the external thread 9 of the threaded wheel 6 shown in FIG. 1 engages when the positioning instrument 1 is being manipulated. Furthermore a nose-shaped guide body 44, which in the installed condition of the positioning instrument 1 engages in the recess 30 of the base 3 stretching in the longitudinal direction of the base 3 to guide the transmission case 10 in the axial direction shown in FIG. 2, is fixed on the inside 43 of the tubular base 40 of the transmission case 10. Thus rotation of the transmission case 10 around the longitudinal axis 22 is prevented.

FIG. 4B shows the transmission case 10 represented in FIG. 4A from the direction designated as IV B. FIG. 4B shows a screw element 45 is represented which joins the guide body 44 with the tubular base 40. In addition the tubular base 40 on its end face 45 has a cylindrical recess 46, into which the spacer 14 can be inserted at its end, in order to allow advantageous support and the transfer of force.

FIG. 5A shows in detail the threaded wheel 6 represented in FIG. 1. The threaded wheel 6 comprises a threaded sleeve 50, on which the external thread 9 is formed. Due to the variable displacement wheel 51 of the threaded wheel 6 advantageous transfer of force to the positioning instrument 1 in order to tighten and loosen the extension shell 2 results. In this case the variable displacement wheel 51 as can be noted particularly well in FIG. 5B, has several recesses 52a to 52f formed ergonomically matching the fingers of a hand, through which a forceful manual grip by hand is also possible and in addition slipping, even in the case of a wet variable displacement wheel 51, is prevented. As the result of the slit-shaped recess 8' the threaded wheel 6 can be installed and dismantled in the vicinity of the faces 7, 8 of the base 3. In the installed condition of the positioning instrument 1 the threaded wheel 6 with the external thread 9 engages in the internal thread 42 of the transmission case 10. When the threaded wheel 6 is turned in the clockwise direction 12 a lifting on the transmission case 10 is produced, which is opposite the direction of insertion 13.

In addition the threaded wheel 6 exhibits the thread 5' formed as trapezoidal thread, which cooperates in the installed condition of the positioning instrument 1 with the thread 5 of the base 3 of the positioning instrument 1. When the threaded wheel 6 is turned in the clockwise direction 12 the threaded wheel 6 is increasingly screwed onto the thread 5, whereby a lifting of the threaded wheel 6 follows in the direction of insertion 13. Since the pitch of the thread 5 or the thread 5' is greater than the pitch of the external thread 9 or the internal thread 42, when the threaded wheel 6 is turned in the clockwise direction 12 a resultant lifting occurs, which adjusts the transmission case 10 in the axial direction along the longitudinal axis 22 in the direction of insertion 13. Thus the resultant lifting of the transmission case 10 in relation to its direction corresponds to the lifting of the threaded wheel 6 relative to the base 3 of the positioning instrument 1. This has the advantage that it is immediately evident to the operating physician, in which direction the transmission case 10 is moved.

Due to the mechanism described a lifting translation device 54 results, which causes the displacement force acting on the spacer 14 to increase. Thus a large displacement force is available for tightening the extension shell 2 by means of the disc element 15 with a rotation of the threaded wheel 6 in the clockwise direction 12, which is transferred via the massively formed threads 5, 5', 9, 42.

As a result of the displacement device 55 comprising the threaded wheel 6, the transmission case 10 and the spacer 14, the force applied by the physician via the threaded wheel 6 is converted to a greater displacement force and this is transferred over a certain distance by means of the spacer 14 onto the disc element 15. Thus insertion of the extension shell 2 into the bone in the direction of insertion 13 is made substantially easier. The disc element 15 in relation to the extension shell 2 fixed on the fixing device 18 is displaced in this case for tightening and loosening the extension shell 2 in the axial direction, that is to say along the longitudinal axis 22, so that the disc element 15, which does not project laterally beyond the tightened extension shell 2 when the extension shell 2 is inserted in the direction of insertion 13 and when the positioning instrument 1 is subsequently removed against the direction of insertion 13, does not remain hanging on the bone or other parts of the body.

The invention is not limited to the embodiment described here.

The invention claimed is:

1. A positioning instrument for inserting an extension shell into a human or animal bone, in particular a pelvic bone, said instrument including a fixing device for attaching the extension shell to the positioning instrument, a displacement device including a disc element at least axially relative to the extension shell, said disc element during an axial displacement contacting beveled surfaces formed interiorly along a perimeter of the extension shell so as to tighten the extension shell and a radial extent of the disc element as viewed in a direction of insertion of the extension shell into said bone, which radial extent is within confines of radially outermost projecting elements of the tightened extension shell, and wherein said disc element includes rotatably mounted rollers which are rollable on said beveled surfaces formed in the extension shell to effectuate a tightening of said extension shell, the displacement device including a screwthreaded wheel for indirectly acting on the disc element, and wherein said screwthreaded wheel includes a lifting translation device for acting on the disc element, wherein said lifting translation device increases an exerting force in a direction of displacement of said disc element, said screwthreaded wheel being connected to a screwthreaded element which is formed on a base of the positioning instrument, said screwthreaded wheel comprising a screwthreaded sleeve having an external screwthread formed on at least axial sections thereof; the screwthreaded sleeve of the screwthreaded wheel having an external screwthread engage in an axially arranged transmission case, whereby upon rotation of the screwthreaded wheel, a lifting displacement of the screwthreaded sleeve operated through the external screwthread is greater than a lifting displacement of the transmission case in an opposite direction responsive to rotation of said external screwthread.

2. A positioning instrument according to claim 1, wherein said fixing device comprises a grub-screw for a screwthreaded engagement with the extension shell.

3. A positioning instrument according to claim 2, wherein said grub-screw is arranged on an end of the positioning instrument facing the direction of insertion of said extension shell.

4. A positioning instrument according to claim 1, wherein said screwthreaded wheel comprises a spacer for acting on the disc element.

5. A positioning instrument according to claim 1, wherein the radially outermost elements about the perimeter of said extension shell comprise a plurality of projections terminating in said beveled surfaces.

* * * * *